(12) United States Patent
Liu et al.

(10) Patent No.: US 7,903,415 B2
(45) Date of Patent: Mar. 8, 2011

(54) AIRFLOW GUIDER FOR USE IN HEAT SINK

(75) Inventors: Ko-Pin Liu, Taipei County (TW); Yue-Ping Dai, Jiangsu (CN)

(73) Assignee: Tai-Sol Electronics Co., Ltd., Taipei (TW)

( * ) Notice: Subject to any disclaimer, the term of this patent is extended or adjusted under 35 U.S.C. 154(b) by 159 days.

(21) Appl. No.: 12/385,645

(22) Filed: Apr. 15, 2009

(65) Prior Publication Data

US 2010/0236754 A1    Sep. 23, 2010

(30) Foreign Application Priority Data

Mar. 17, 2009   (TW) .............................. 98204201 U

(51) Int. Cl.
*H05K 7/20*   (2006.01)
*G06F 1/20*   (2006.01)

(52) U.S. Cl. ............... 361/710; 361/679.47; 361/679.48; 361/679.5; 361/679.51; 361/679.52; 361/679.54; 361/695; 361/697; 361/700; 361/704; 361/709; 361/719; 165/80.3; 165/185; 174/15.2; 174/16.1; 174/16.3

(58) Field of Classification Search .............. 361/679.46–679.52, 679.54, 690, 361/694–695, 697, 700, 703–704, 709–710, 361/719; 165/80.2–80.3, 104.33, 185; 174/15.2, 174/16.1, 16.3
See application file for complete search history.

(56) References Cited

U.S. PATENT DOCUMENTS

| | | | | |
|---|---|---|---|---|
| 4,790,374 | A * | 12/1988 | Jacoby | 165/185 |
| 6,130,820 | A * | 10/2000 | Konstad et al. | 361/695 |
| 6,304,445 | B1 * | 10/2001 | Bollesen | 361/697 |
| 6,989,988 | B2 * | 1/2006 | Arbogast et al. | 361/695 |
| 7,120,018 | B2 * | 10/2006 | Shen et al. | 361/695 |
| 7,204,750 | B2 * | 4/2007 | Shen et al. | 454/184 |
| 7,215,548 | B1 | 5/2007 | Wu et al. | |
| 7,277,281 | B1 * | 10/2007 | Lu et al. | 361/695 |
| 7,349,212 | B2 * | 3/2008 | Xia et al. | 361/697 |
| 7,363,963 | B2 * | 4/2008 | Wang et al. | 165/80.3 |
| 7,403,389 | B2 * | 7/2008 | Yao et al. | 361/695 |
| 7,411,786 | B2 * | 8/2008 | Wang et al. | 361/695 |
| 7,443,679 | B2 * | 10/2008 | Li et al. | 361/704 |
| 7,447,028 | B2 * | 11/2008 | Lai et al. | 361/697 |
| 7,532,468 | B2 * | 5/2009 | Sun et al. | 361/690 |
| 7,663,882 | B2 * | 2/2010 | Li et al. | 361/697 |
| 7,665,509 | B2 * | 2/2010 | Tung et al. | 165/104.26 |
| 7,760,498 | B2 * | 7/2010 | Shan et al. | 361/695 |
| 2007/0058341 | A1* | 3/2007 | Hsiao | 361/695 |
| 2008/0151498 | A1* | 6/2008 | Zhang | 361/697 |
| 2010/0149749 | A1* | 6/2010 | Cao et al. | 361/679.47 |
| 2010/0172089 | A1* | 7/2010 | Chiu et al. | 361/679.47 |

FOREIGN PATENT DOCUMENTS

JP          10012781 A   *   1/1998

* cited by examiner

*Primary Examiner* — Robert J Hoffberg
(74) *Attorney, Agent, or Firm* — Bacon & Thomas, PLLC

(57) ABSTRACT

An airflow guider includes a plate-like member having a stop portion extending transversely, a rear inclined guiding portion extending downward rearward toward a first side from a top edge of the stop portion, a front inclined guiding portion extending slantwise forward toward the first side from the stop portion, and at least one fixture for installing the airflow guider to a heat sink. In light of the structure, the airflow guider can be coordinately installed to various kinds of heat sinks and provide additional thermal dissipation.

5 Claims, 5 Drawing Sheets

AIRFLOW GUIDER FOR USE IN HEAT SINK

BACKGROUND OF THE INVENTION

1. Field of the Invention

The present invention relates generally to thermal dissipation, and more particularly, to an airflow guider for use in a heat sink.

2. Description of the Related Art

U.S. Pat. No. 7,215,548 disclosed a heat dissipating device composed of a heat spreader, a plurality of first fins, and a fan. The first fins include a guiding fin having a body and an inclined sidewall bent from the body, for guiding the airflow generated by the fan.

When the heat dissipating device is operated and the airflow of the fan passes through under the guiding fin to flow outside, the airflow is guided by the inclined sidewall to flow downward in such a way that the airflow can flow to heating elements located on a circuit board or motherboard below the inclined sidewall. In this way, the heat dissipating device can provide thermal dissipation for not only a CPU of a computer but also heating elements in the proximity of the CPU. Besides, as can be seen from FIG. 3 of the '548 patent, the guiding fin further includes a bottom edge located at a bottom lateral side thereof for blocking a part of the airflow located at the bottom side of the guiding fin and for interfering it and then guiding it to flow downward. In this way, the airflow can be blown by the fan down to heating elements located below the bottom side of the guiding fan.

However, the guiding fin must be assembled with the first fins together, such that it limits the assembly of the guiding fin. In other words, the guiding fin fails to be singly assembled with other types of the heat sink.

SUMMARY OF THE INVENTION

The primary objective of the present invention is to provide an airflow guider, which can be assembled with different heat sinks.

The secondary objective of the present invention is to provide an airflow guider, which guides the airflow toward other heating elements for additional thermal dissipation.

The foregoing objectives of the present invention are attained by the airflow guider composed of a plate-like member. The plate-like member includes a stop portion extending transversely, a rear inclined guiding portion extending downward rearward toward a first side from a top edge of the stop portion, a front inclined guiding portion extending slantwise forward toward the first side from the stop portion, and at least one fixture for installing the airflow guider to a heat sink.

DETAILED DESCRIPTION OF PREFERRED EMBODIMENTS

Figure 1:
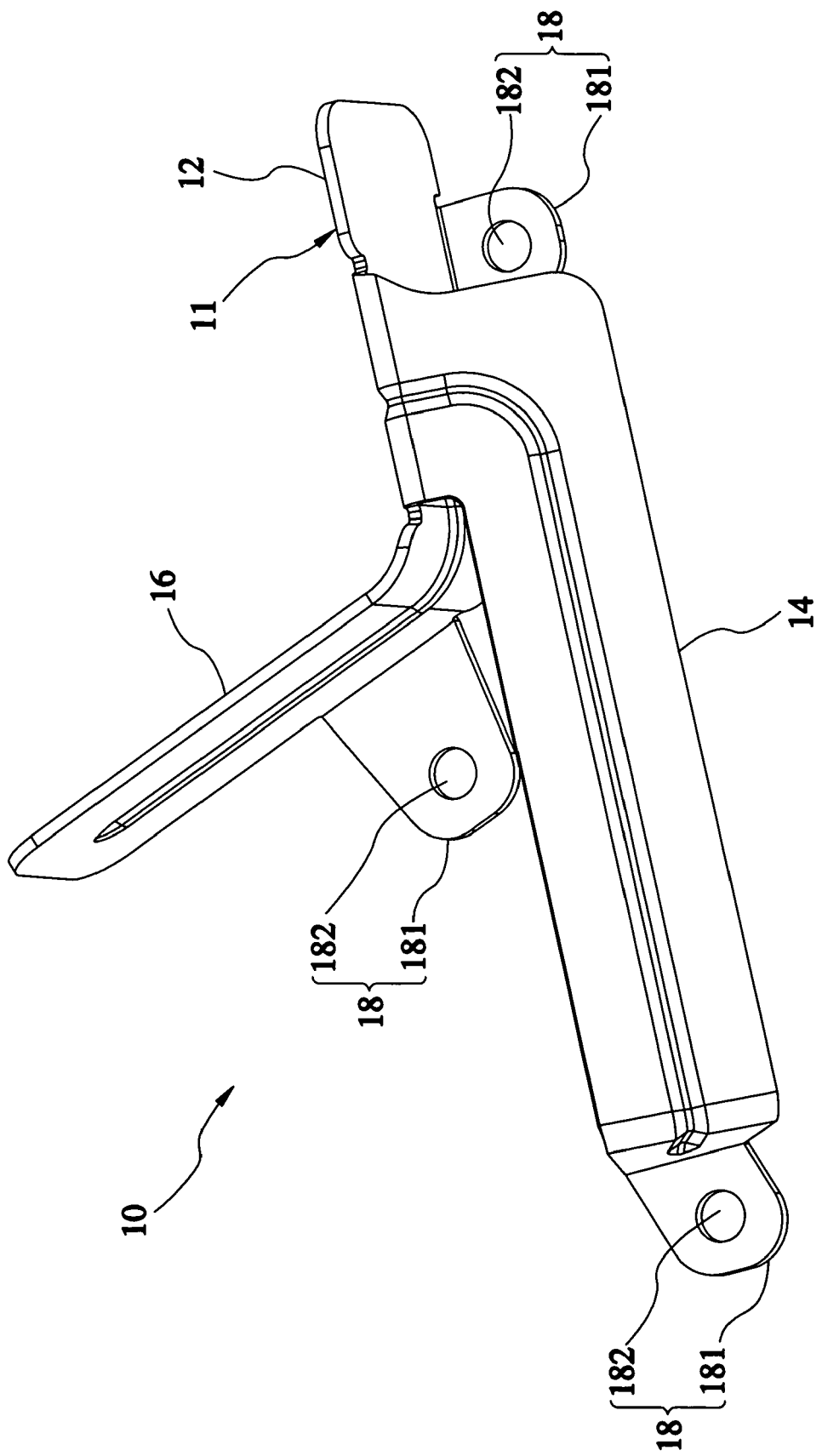
FIG. 1 is a perspective view of a preferred embodiment of the present invention.

Referring to FIG. 1, an airflow guider 10 for use in a heat sink in accordance with a preferred embodiment of the present invention is composed of a plate-like member 10.

The plate-like member 10 includes a stop portion 12 extending transversally, a rear inclined guiding portion 14 extending downward rearward toward a first side (left side) for a predetermined length from a top edge of the stop portion 12, and a front inclined guiding portion 16 extending forward toward the first side for a predetermined length from the stop portion 12. The front inclined guiding portion 16 has a distal end whose shadow can be projected onto the rear inclined guiding portion 14 to be located at a midsection of the rear inclined guiding portion 14.

Figure 2:
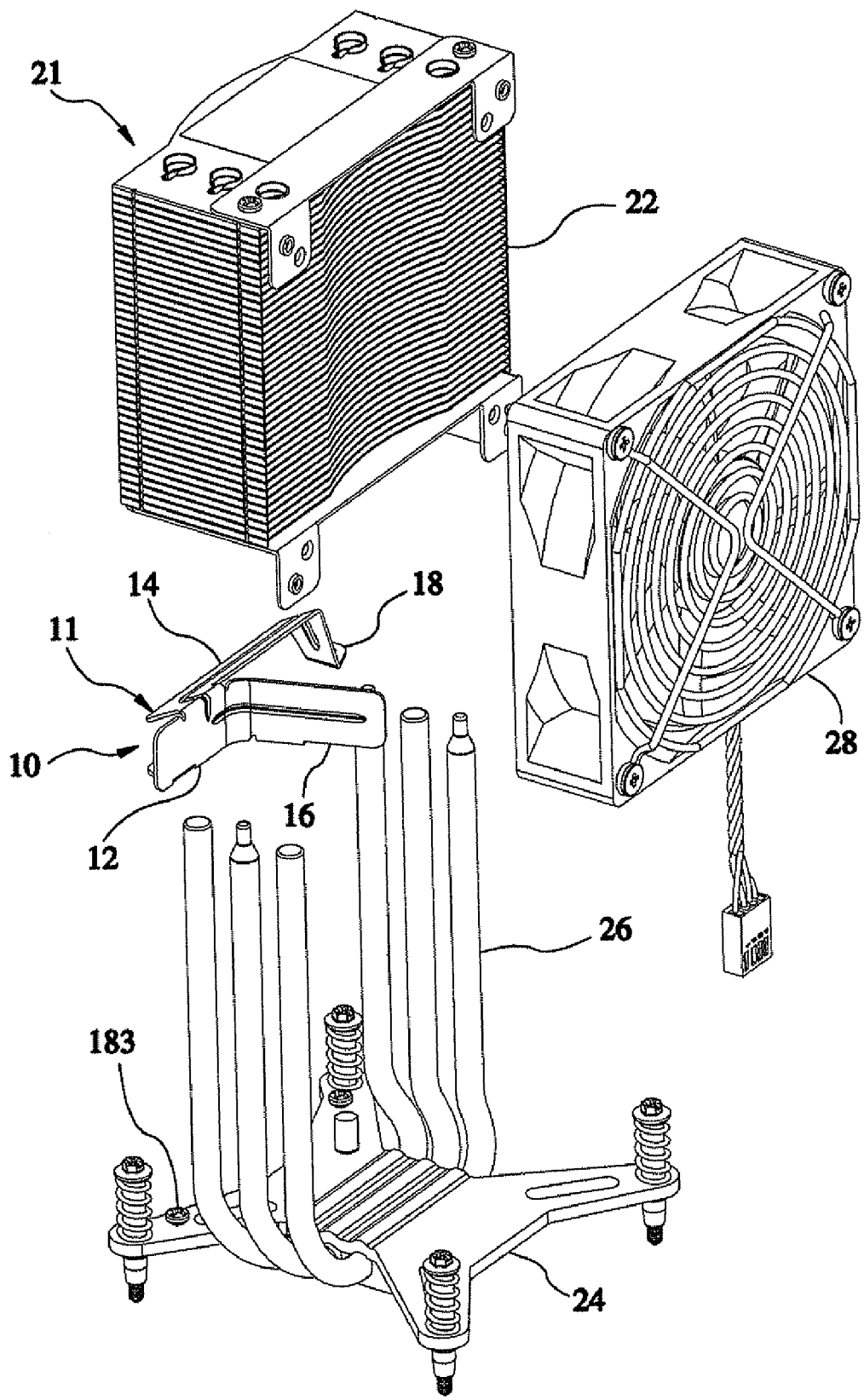
FIG. 2 is another perspective view of the first preferred embodiment of the present invention before assembled with a heat sink.
Figure 3:
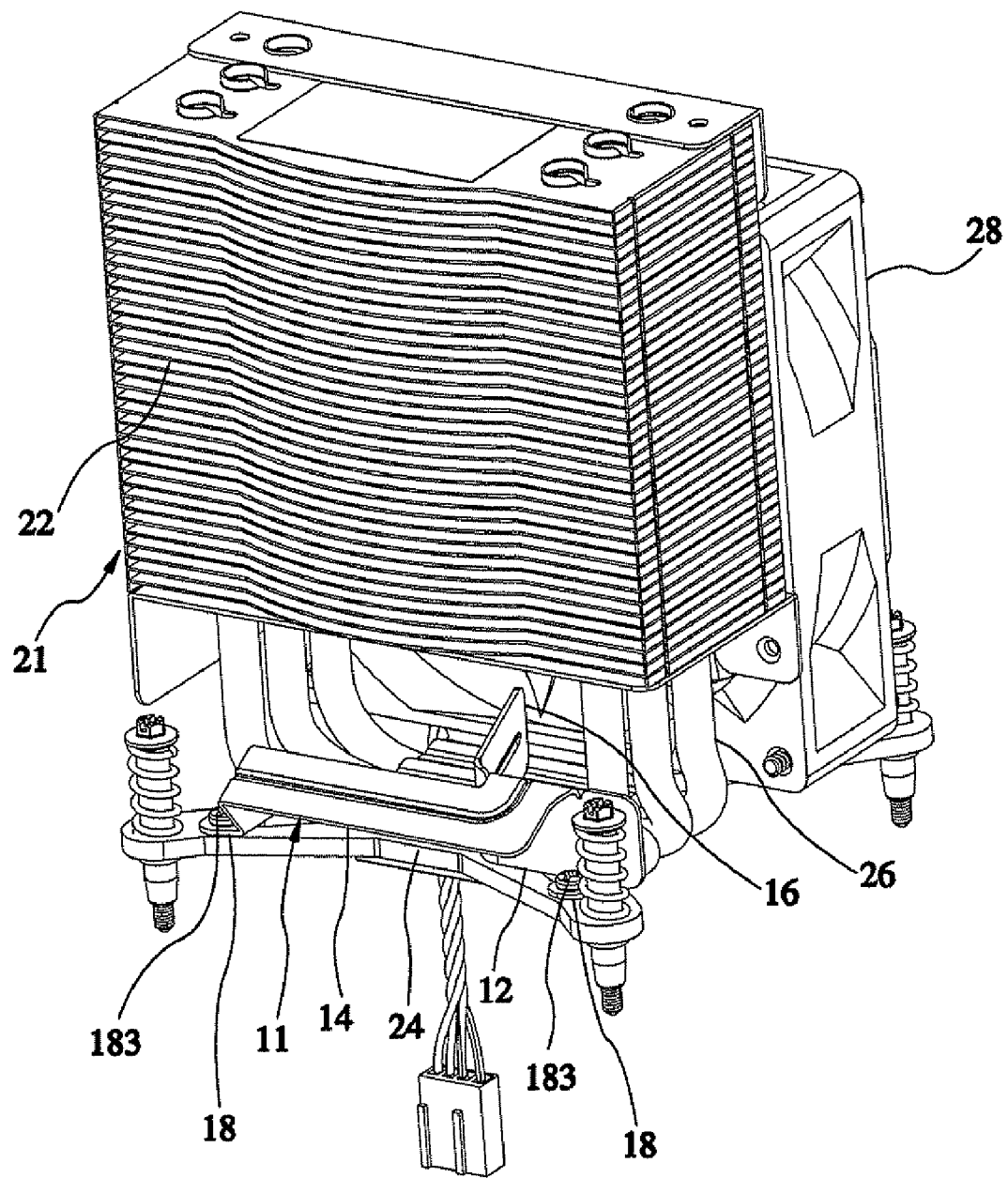
FIG. 3 is a perspective view of the first preferred embodiment of the present invention assembled with the heat sink.
Figure 4:
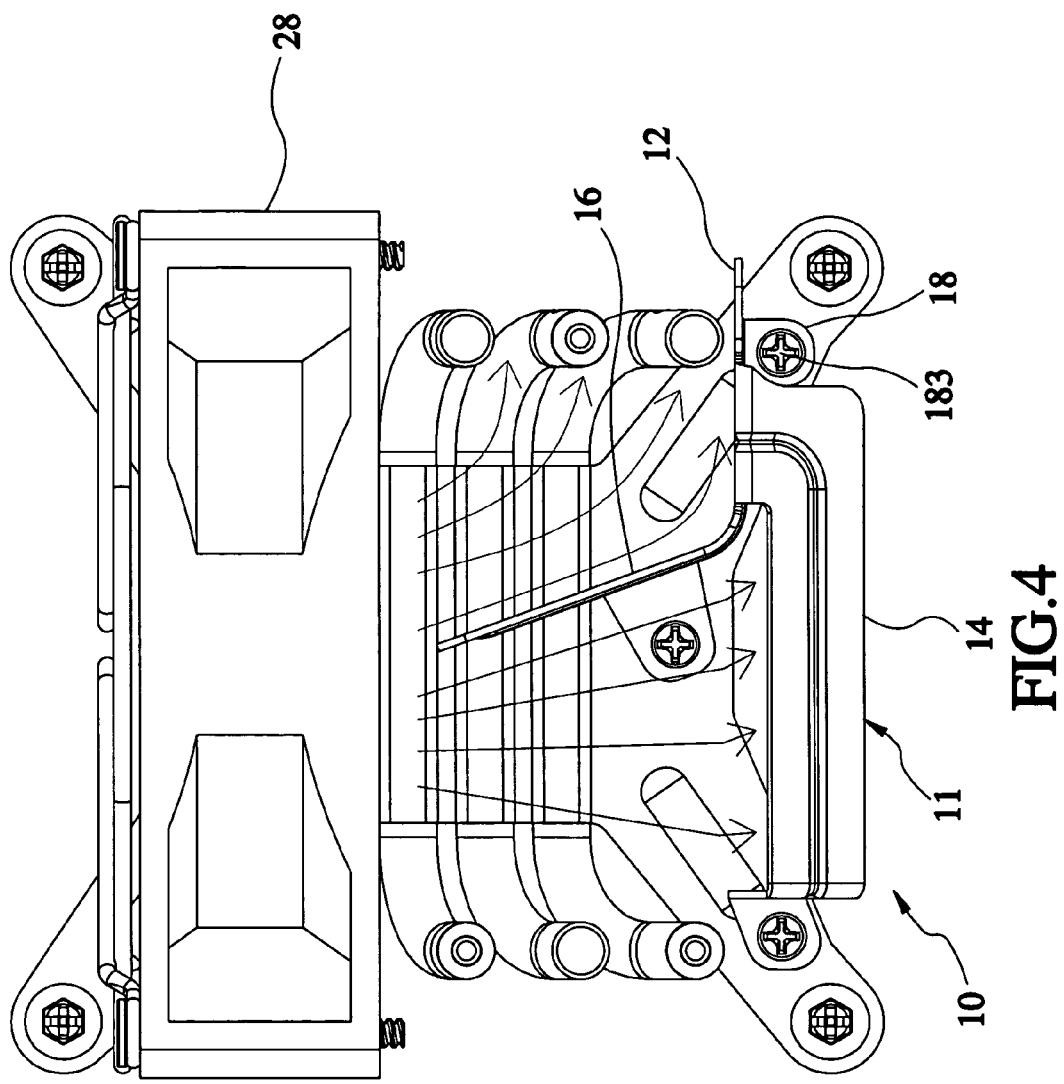
FIG. 4 is a schematic view of the first preferred embodiment of the present invention, illustrating that the paths of airflow generated by the fan and guided by the present invention.

The plate-like member 10 includes three fixtures 18 located at the stop portion 12, the rear inclined guiding portion 14, and the front inclined guiding portion 16 respectively, for installing itself coordinately to a heat sink 21, as shown in FIGS. 2-4. Each of the fixtures 18 is a lug in this embodiment, having a through hole 182 running therethrough for a screw 183 shown in FIG. 3 to pass through.

When airflow is blown toward the front side of the air guider 10, the airflow is interfered by the front inclined guiding portion 16 to branch; then one part of the airflow is guided by the front inclined guiding portion 16 to flow sideward, i.e. rightward in FIG. 1, and the other part is not guided by the front inclined guiding portion 16 to flow rearward but guided by the rear inclined guiding portion 14 to flow slantwise downward outward.

Figure 5:
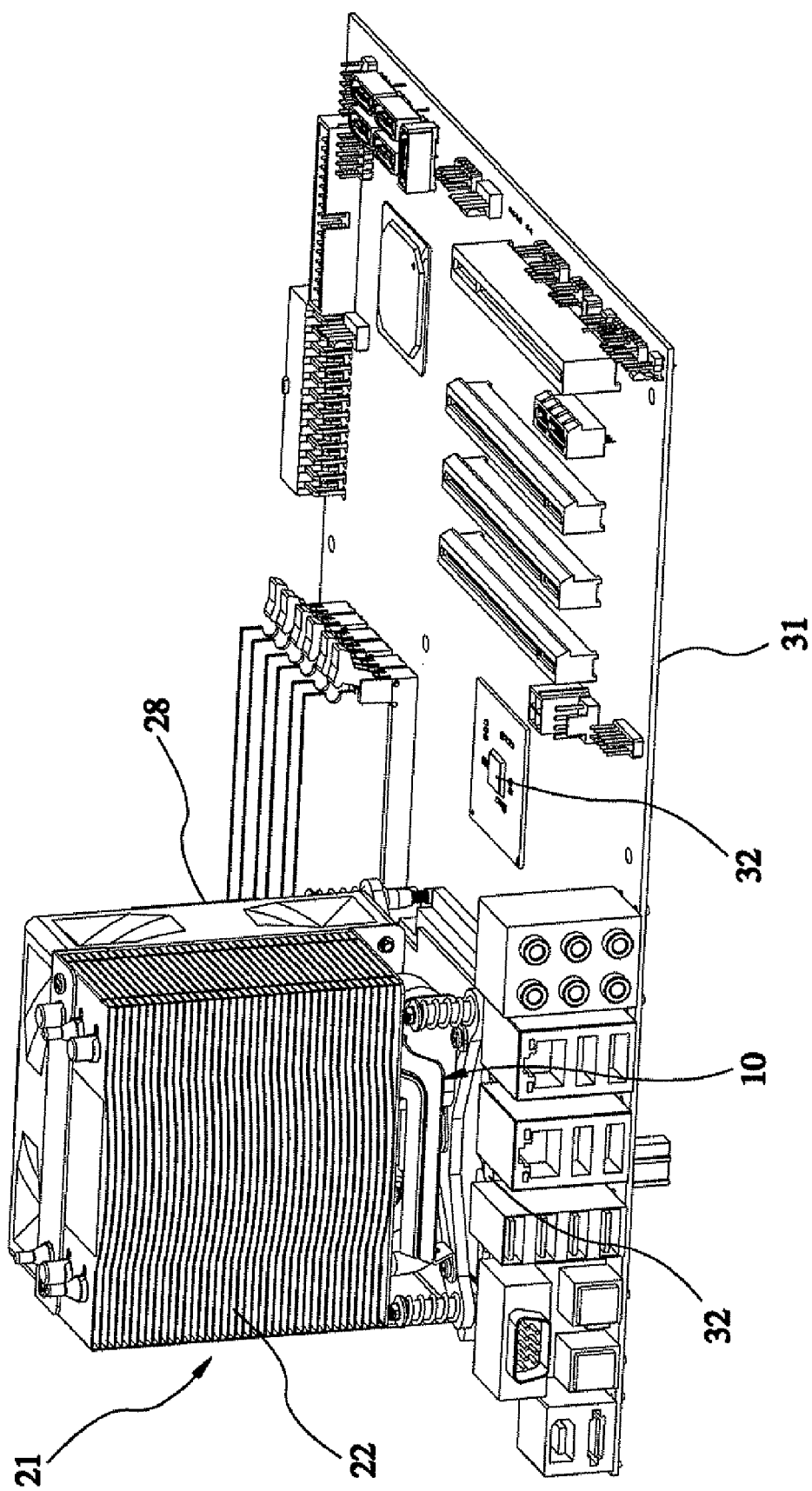
FIG. 5 is another perspective view of the preferred embodiment of the present invention mounted to a circuit board.

Referring to FIGS. 2-3 again, the heat sink 21 is composed of a plurality of fins 22, a heat-dissipating plate 24 mounted below the fins 22, a plurality of heat pipes 26 running through the fins 22 and connected with the heat-dissipating plate 24, and a fan 28 mounted beside the fins 22 and the heat-dissipating plate 24. The airflow guider 10 of the present invention is fixed mounted onto the heat-dissipating plate 24 by the screw 183 and located at an opposite side of the heat-dissipating plate 24 with respect to the fan 28. When the heat sink 21 is operated, the airflow generated by the fan 28 passes through the fins 22 to take away the heat of the fins 22 for thermal dissipation. As shown in FIG. 4, the paths of the airflow of the fan 28 are marked with arrows. Some of the airflow passes through the bottom side of the fins 22 to be guided by the airflow guider 10 and to further generate two branches, one of which flows sideward and the other flows rearward downward. Referring to FIG. 5, when the heat sink 21 as well as the airflow guider 10 is mounted to a circuit board 31, the branch flowing sideward can be provided for thermally dissipating heating elements 32 located on the circuit board 31 and beside the heat sink 21, and the branch flowing rearward downward can be provided for the heating elements located on the circuit board 31 and behind the heat sink 21.

In conclusion, the present invention includes the following advantages and effects.

1. The present invention can assist the heat sink located below the fins in guiding the airflow. Besides, the airflow guider of the present invention is installed independently onto the heat sink, such that the present invention is applicable to a variety of heat sinks each having an airflow channel located thereunder. Therefore, the present invention indeed improves the limited assembly of the prior art.

2. The present invention can guide the airflow to flow toward one side and downward in such a way that the airflow can be additionally blown to other heating elements on the circuit board for thermal dissipation. Besides, the sidewardly guiding thermal dissipation of the present invention is different from the conventional thermal dissipation of the prior art because the lateral side of the present invention is open and the prior art's is closed to enable the airflow to flow downward. Therefore, the airflow in the prior art covers less area than in the present invention and the lateral side of the present invention is more efficient than that of the prior art in thermal dissipation.

Although the present invention has been described with respect to a specific preferred embodiment thereof, it is no way limited to the details of the illustrated structures but changes and modifications may be made within the scope of the appended claims.

What is claimed is:

1. An airflow guider for use in a heat sink, comprising
   a vertical stop portion having a top edge and a side edge, the vertical stop portion extending transversally away from the side edge in a first direction towards a first side of the airflow guider;
   a rear inclined guiding portion extending rearward and downward from the top edge of the vertical stop portion, the rear inclined guiding portion extending in a second direction towards a second side of the airflow guider, the second side being opposite to the first side;
   a vertical front inclined guiding portion extending forward and slantwise away from the side edge of the vertical stop portion in a third direction towards the second side of the airflow guider; and
   at least one fixture for installing the airflow guider coordinately to the heat sink,
   wherein the airflow guider is a plate-like member of substantial uniform thickness.

2. The airflow guider as defined in claim 1, wherein the vertical front inclined guiding portion comprises a distal end, a shadow of the distal end being projected onto a midsection of the rear inclined guiding portion.

3. The airflow guider as defined in claim 1, wherein the at least one fixture is a lug having a through hole.

4. The airflow guider as defined in claim 1, wherein the at least one fixture is three fixtures, the three fixtures are located at the vertical stop portion, the rear inclined guiding portion, and the vertical front inclined guiding portion respectively.

5. The airflow guider as defined in claim 1, wherein the second side is a left side or a right side.

* * * * *